United States Patent [19]

Meiattini

[11] Patent Number: 5,183,762
[45] Date of Patent: Feb. 2, 1993

[54] COPPER CONTAINING REAGENT FOR THE DETECTION AND DETERMINATION OF BILIRUBIN IN THE URINE

[75] Inventor: Franco Meiattini, Siena, Italy

[73] Assignee: Diesse Diagnostica Senese S.R.L., Milan, Italy

[21] Appl. No.: 544,599

[22] Filed: Jun. 27, 1990

[30] Foreign Application Priority Data

Sep. 21, 1989 [IT] Italy .................. 21789 A/89

[51] Int. Cl.$^5$ ............... G01N 21/78; G01N 33/72
[52] U.S. Cl. ................... 436/97; 436/166; 436/903
[58] Field of Search ............ 436/97, 166, 903

[56] References Cited

U.S. PATENT DOCUMENTS

| | | | |
|---|---|---|---|
| 2,737,501 | 3/1956 | Sherman | 436/97 |
| 4,038,031 | 7/1977 | Lam | 436/97 |
| 4,404,286 | 9/1983 | Shull | 436/97 |
| 4,965,210 | 10/1990 | Modrovich | 436/903 X |

FOREIGN PATENT DOCUMENTS

| | | | |
|---|---|---|---|
| 0217197 | 4/1987 | European Pat. Off. | |
| 2215869 | 8/1974 | France | 436/97 |
| 0160764 | 9/1984 | Japan | 436/97 |
| 3118662 | 5/1988 | Japan | 436/97 |

OTHER PUBLICATIONS

Michaelsson, *The Scandinavian Journal of Clinical & Laboratory Investigation*, (1961), 13, "Bilirubin Determination in Serum and Urine. Studies on Diazol..." Oslo.

*Primary Examiner*—Robert J. Hill, Jr.
*Attorney, Agent, or Firm*—Oblon, Spivak, McClelland, Maier & Neustadt

[57] ABSTRACT

A reagent containing a buffer suitable for maintaining the Ph of the reagent between 3–7, sulfanilic acid or sulfanilamide, a cupric soluble salt and an alkaline metal nitrite, for the detection and determination of bilirubin in the urine providing precise results and ready automation of the procedure, characterized in that it is a stable combination of all the substances used for such analysis.

12 Claims, No Drawings

COPPER CONTAINING REAGENT FOR THE DETECTION AND DETERMINATION OF BILIRUBIN IN THE URINE

BACKGROUND OF THE INVENTION

1. Field of the Invention

The present invention relates to a novel reagent useful for the detection and determination of bilirubin in the urine.

2. Discussion of the Background

At present the detection and determination of bilirubin in body fluids can be carried out according to three methods:
a) the spectrophotometric method by direct reading of the yellow pigment of bilirubin. Obviously such a method cannot be employed for the determination in the urine as the color of the fluid is often the same of the pigment;
b) the enzymatic method employing bilirubin oxidase: the oxidized bilirubin loses the yellow color, hence its concentration can be assessed by a decease in absorbance; also this method is not generally used in determinations in the urine;
c) the chemical method by diazo-coupling between a diazotized aromatic compound (diazo compound) and bilirubin: this method exhibits the highest sensitivity as well as economical advantages.

The diazo-coupling between bilirubin and a suitable diazo compound yields the formation of azobilirubin, a substance behaving like a pH indicator, in fact it turns red in neutral or slightly acidic solution, blue in highly alkaline solution, and purple in very acidic solution.

The determination of bilirubin in the urine gives completely different problems with respect to the determination in the serum. In this latter biological fluid, bilirubin is both in free and in conjugate form, i.e. in the form of a glucuronic acid salt. These two forms show a different reactivity to diazo compounds. The free bilirubin is less prone to the diazo-coupling that accordingly takes place only in the presence of suitable accelerators. From the clinical point of view it is important to determine the concentration of both of the forms in the serum, and also the ratio between them.

In the urine, bilirubin is essentially in conjugated form, hence it is not necessary to employ accelerators for the diazo-coupling. However the quantitative determination in this fluid is unsatisfactory because the many and different substances present bring about interferences both in the photometric reading and by directly reacting with the diazo compound and yielding aspecific colors.

In order to make this kind of analysis more faithful, accurate and reproducible, modifications to both the stability and the sensitivity of the reagents, as well as the analytic procedure have been tried.

As known, the diazo compounds are usually unstable. Attempts have been made to eliminate this drawback by employing their complexes with zinc salts (the so-called Fast Red RC, Fast Red PDC, and so on).

Unfortunately these compounds proved to be unemployable for the determination of bilirubin in the urine as they react also with the urobilinogen, a substance always present in the urine even if in undetermined amounts. Furthermore the diazo compounds can give rise to aspecific colorings by reacting with medicaments and/or metabolites thereof.

Another problem arises from the extreme variability of the urine appearance and color. These characteristics may undergo noticeable changes by adding the strongly acidic reagent. The sudden lowering of pH, for example, can cause the precipitation of substances such as uric acid, only slightly soluble in acidic environments.

For reducing such interferences an attempt has been made to alkalize the sample after the reagent addition, just like in the procedure for the serum, so as to make azobilirubin turn blue from red. This renders the determination more specific as few interfering substances provide blue colorings.

Nevertheless, this technique is inconvenient since azobilirubin is stable in alkaline environment only in the presence of proteins and it is known that, excepting for pathologic situations, proteins are always absent in the urine. It follows that the instability of the bilirubin pigment makes the results totally unfaithful.

Also, advantage has been taken of the fact that azobilirubin yields colored complexes together with metallic ions such as $Co^{3+}$, $Cu^{2+}$ and $Ni^{2+}$. Particularly, the formation of the azobilirubin-$Cu^{2+}$ complex described, amoung the others, by Michaelsson M., in Scand. J. Clin. Lab. Invest., 13, Suppl. 56, 1 (1961) permits one to obtain a blue reaction product also in the absence of alkaline substances. As already mentioned above, the blue color permits one to carry out photometric readings at wavelengths at which other pigments are not interfering at all. It is known that, while azobilirubin is red and has an absorption peak at 530–550 nm in neutral or slightly acidic environment, the azobilirubin-$Cu^{2+}$ complex is blue and has an absorbance peak at 615–620 nm at a pH ranging between 3.8 and 11. At pHs lower than 3.8, the blue color progressively turns red and the peak at 615 nm decreases until it disappears, and finally the color turns pure red with an absorbance peak at 535 nm at pH 2.4. This leads to the supposition that the azobilirubin-$Cu^{2+}$ complex is stable only at a pH ranging between 3.8 and 11, and at pHs lower than 3.8 it dissociates more and more until it appears completely dissociated at pH 2.4.

The reason for the Michaelsson's choice of pH=6 for the diazo-coupling method and subsequent formation of the blue complex with $Cu^{2+}$ for the determination of bilirubin in the urine follows from these observations.

This technique however shows noticeable disadvantages with regard to the practicality and, above all, the automation of the analysis. In fact, the technique involves the use of four different reagents and accordingly of four reactions for each tested sample ("copper sample", "copper blank", "water sample" and "water blank") with consequent data evaluation for each reaction, and reaction times (about 10 minutes) too long for analysis laboratories which have to analyze hundreds of samples a day.

SUMMARY OF THE INVENTION

One object of the invention is to improve and simplify the analysis method according to Michaelsson by providing a reagent which is able to provide precise and faithful results devoid of possible interferences with the substances present in the sample, and in the meantime being handy and stable over time.

These and other objects are attained by the present reagent containing an aromatic compound susceptible to diazo reaction, a soluble cupric salt, a buffer suitable to maintain the pH between 3 and 7 and inert to cupric ions, and an alkali metal nitride that may be part of the above-mentioned mixture or may be added to the mixture at the moment of the determination.

Optionally but preferably, such composition also comprises one or more anionic and no-ionic surfactants (or detergents), and dimethylsulfoxide (DMSO)

DETAILED DESCRIPTION OF THE PREFERRED EMBODIMENTS

The reagent according to the present invention preferably comprises the buffer preferably in a concentration between 10 mmol/l and 5,000 mmol/l, the suitable aromatic compound in a concentration between 5 mmol/l and 200 mmol/l, the cupric salt in a concentration between 1 mmol/l and 30 mmol/l and the nitrite in a concentration between 10 mmol/l and 1,000 mmol/l. Still more preferably, the buffer is in a concentration of about 3,000 mmol/l, the suitable aromatic compound is in a concentration of about 150 mmol/l, the cupric salt is in a concentration of about 5 mmol/l and the nitrite is in a concentration of about 45 mmol/l.

The surfactant or mixture thereof is in a concentration between 0% and 10% w/v, preferably in a concentration of about 0.3% w/v.

DMSO is in a concentration between 0% and 100% w/v preferably in a concentration of about 50% w/v.

Surprisingly it has been found that it is not necessary to add $Cu^{2+}$ necessary to form the azobilirubin-$Cu^{2+}$ complex at the end of the diazo-coupling, as described by Michaelsson, rather $Cu^{2+}$ may be pre-mixed in a single reagent also consisting of all of the above-mentioned compounds, and optionally the nitrite which acts as an initiator of the series of reactions yielding the formation of the azobilirubin-$Cu^{2+}$ blue complex.

It has also been surprisingly found, in contrast to what is taught by the prior art relating the diazo-coupling at strongly acidic pH, that the aromatic compound susceptible of diazo reaction may be added to the reagent at a from weakly acidic to neutral pH maintained stable by a buffer, together with $Cu^{2+}$ and optional surfactants useful to rapidly clarify some peculiar kinds of sample.

Surprisingly, it was also found that the azobilirubin-$Cu^{2+}$ complex completely forms at pHs lower than 3.8, even if in such conditions it rapidly dissociates. At such pHs the "surviving" time of the complex is sufficient to carry out the photometric reading useful for determining bilirubin. The importance of the use of pH=3 lies in the fact that at such pH a rapid solubilization of calcium and magnesium phosphates is achieved, as such salts frequently precipitate in the urine samples at neutral or alkaline pH and make the same turbid.

DMSO may be employed to slow down the formation of the azobilirubin-$Cu^{2+}$ complex according to a principle completely different from the known one whereby DMSO is solely employed as an accelerator in the determination of free bilirubin in the serum. DMSO forms coordination complexes with copper and other metals, and it was also found that this characteristic may be exploited in the present reagent for making $Cu^{2+}$ more or less directly disposable for the formation of the azobilirubin-$Cu^{2+}$ complex, with the consequent possibility of modulating the formation speed of the complex itself. Such a possibility is mainly useful when the analysis is manually carried out, i.e. when it takes slower reaction times for reading the data.

Additionally, the present reagent for the detection and determination of bilirubin in the urine has proven to be advantageous for the shortness of the analysis times and the total possibility of automation.

The present reagent surprisingly combines all the substances useful for detecting and determining bilirubin in the urine, therefore providing an analytic instrument extremely simple, faithful and handy. Furthermore, by subdividing the active components into two reagents the first containing nitrite and optionally DMSO, and the second the buffer, the aromatic compound susceptible to diazo reaction, $Cu^{2+}$ and optional surfactants, the reagents remain stable for over one year at room temperatures.

The two reagents may be admixed before use to form a single reagent having less stability, but more than sufficient stability to permit a number of determinations within the period of time necessary for carrying out a regular analytic procedure. Taking into account that it is possible to carry out an analysis in a few seconds by the system disclosed, the use of the single reagent allows the analysis of at least 700 samples/h, especially if it is coupled with rapid automatic apparatus. Such an operative speed is undoubtely higher than the one reached in the majority of the analysis laboratories.

Alternatively, the use of two separated reagents obviates any stability problem as the two reagents may also be left in the automatic apparatus providing separate containers for placing the reagents. Also in this case the extremely high reaction speed obtainable with the described reagents allows one to analyze from over 350 samples/h up to at least 700 samples/h.

In the tests carried out for optimizing the different components, particular attention was paid to the choice of the buffer and the concentration of $Cu^{2+}$. In fact, it has been seen that too low of a concentration of cupric ions causes a loss of sensitivity as they are insufficient to the complete formation of the complex with azobilirubin. Conversely, too high of a concentration makes the complex and the resulting color unstable. It follows therefrom that the concentration of $Cu^{2+}$ suitably employed in the present reagent ranges from 1 to 10 mmol/l.

Among the buffers tested ap pHs ranging from 3 and 7, citrate and succinate did not prove to be suitable. Citrate chelates and takes $Cu^{2+}$ away from the formation of the complex with azobilirubin, and succinate causes the precipitation of the corresponding cupric salt. Suitable buffer have been found to be acetic acid-sodium acetate, glycine-HCl and formate-HCl, although any buffer system may be employed provided that it does not yield insoluble salts, chelates or cupric complexes.

Among the additives, besides the already cited DMSO, the surfactants (or detergents) have proven to be surprisingly useful. As already previously mentioned, they are particularly useful to rapidly clarify some peculiar kinds of samples. An example is when the urine contains a large number of leukocytes, erythrocytes or other cells which provide it with a particularly lactescent or turbid appearance. In the absence of surfactants it may happen that the turbidity of the sample noticeably thwarts the photometric reading by opposing the passing of light. Also it may happen, and this is the most frequent and harmful event because it is less controllable, that when sample and reagents are admixed, a slow cell lysis gives rise to a gradual decrease of the mixture turbidity with consequent decrease of absorbance. Such a negative variation can give rise to negative errors by superimposition on the positive variation due to the specific colored reaction of bilirubin. The addition of surfactants to the reactive mixture causes a very fast cell lysis and the clarification of the mixture takes place before the specific colored reaction of bilirubin.

For making the features of the present invention more clear, the following description shows some non-limiting examples of the invention.

EXAMPLES

Example 1

A reagent A was prepared containing 80 mmol/l of sulfanilic acid, 300 mmol/l of glycine-HCl buffer so that the pH=4.5, 12 mmol/l of $Cu^{2+}$ and 0.1% w/v Triton X-67® (an octylphenoxy polyethoxyethanol surfactant) (Rohm & Haas Co.). Separately a reagent B containing 45 mmol/l of $NaNO_2$ in water was prepared. The reagents A and B were admixed before use in equal parts (single reagent C). The samples were taken from a pool of normal urines to which ditaurate bilirubin at concentrations of 0, 0.31, 0.62, 1.25, 2.5, 5, 10, and 20 mg/dl was added.

In a spectrophotometric cuvette 2 ml of water and 0.5 ml of the test sample were admixed. The first photometric reading ($A_1$) was carried out at 635 nm, then 1 ml of single reagent C was added. Five seconds after the addition of reagent C, a second photometric reading ($A_2$) was carried out always at 635 nm. The difference between the two readings ($A_2-A_1$) was correlable to the concentration of bilirubin, at least up to 20 mg/dl as shown in the following Table 1.

TABLE 1

| ditaurate bilirubin (mg/dl) | $A_1$ | $A_2$ | $A_2$-$A_1$ |
|---|---|---|---|
| 0.00 | 0.149 | 0.149 | 0.000 |
| 0.31 | 0.155 | 0.168 | 0.013 |
| 0.62 | 0.143 | 0.164 | 0.021 |
| 1.25 | 0.149 | 0.187 | 0.038 |
| 2.50 | 0.149 | 0.222 | 0.073 |
| 5.00 | 0.152 | 0.305 | 0.153 |
| 10.00 | 0.146 | 0.456 | 0.310 |
| 20.00 | 0.146 | 0.745 | 0.599 |

Example 2

A reagent A was prepared containing 80 mmol/l of sulfanilic acid, 300 mmol/l of glycine-HCl buffer so that the pH=4.5, 12 mmol/l of $Cu^{2+}$ and 0.1% w/v Triton X-67® (an octylphenoxy polyethoxyethanol surfactant) (Rohm & Haas Co.). Separately a reagent B containing 45 mmol/l of $NaNO_2$ in 50% of DMSO v/v in water was prepared. The reagents A and B were admixed before use in equal parts (single reagent C). The samples were taken from a pool of normal urines to which ditaurate bilirubin at concentrations of 0, 0.31, 0.62, 1.25, 2.5, 5, 10, and 20 mg/dl was added.

In a spectrophotometric cuvette 2 ml of water and 0.5 ml of the test sample were admixed. The first photometric reading ($A_1$) was carried out at 635 nm, then 1 ml of single reagent C was added. 30 seconds after the addition of reagent C, a second photometric reading ($A_2$) was carried out always at 635 nm. The difference between the two readings ($A_2-A_1$) was correlable to the concentration of bilirubin, at least up to 20 mg/dl as shown in the following Table 2.

TABLE 2

| ditaurate bilirubin (mg/dl) | $A_1$ | $A_2$ | $A_2$-$A_1$ |
|---|---|---|---|
| 0.00 | 0.174 | 0.174 | 0.000 |
| 0.31 | 0.180 | 0.192 | 0.012 |
| 0.62 | 0.178 | 0.202 | 0.024 |
| 1.25 | 0.174 | 0.225 | 0.051 |
| 2.50 | 0.190 | 0.288 | 0.098 |
| 5.00 | 0.177 | 0.372 | 0.195 |
| 10.00 | 0.190 | 0.509 | 0.319 |
| 20.00 | 0.187 | 0.721 | 0.534 |

Example 3

A reagent A was prepared containing 10 mmol/l of sulfanilamide, 500 mmol/l of sodium formate-HCl buffer so that the pH=3.6, 3 mmol/l of $Cu^{2+}$ and 0.05% w/v Brij-35® (a polyoxyethylene alcohol surfactant) (Atlas Chemical Industries Inc.). Separately a reagent B containing 500 mmol/l of $NaNO_2$ in water was prepared. The samples were taken from a pool of normal urines to which ditaurate bilirubin at concentrations of 0, 0.31, 0.62, 1.25, 2.5, 5, 10, and 20 mg/dl was added.

In a spectrophotometric cuvette 1 ml of water, 0.5 ml of the test sample and 2 ml of reagent A were admixed. The first photometric reading ($A_1$) was carried out at 615 nm, then 0.05 ml of reagent B was added. Five seconds after the addition of reagent B, a second photometric reading ($A_2$) was carried out always at 615 nm. The difference between the two readings ($A_2-A_1$) was correlable to the concentration of bilirubin, at least up to 20 mg/dl as shown in the following Table 3.

TABLE 3

| ditaurate bilirubin (mg/dl) | $A_1$ | $A_2$ | $A_2$-$A_1$ |
|---|---|---|---|
| 0.00 | 0.067 | 0.068 | 0.001 |
| 0.31 | 0.067 | 0.078 | 0.011 |
| 0.62 | 0.072 | 0.093 | 0.021 |
| 1.25 | 0.074 | 0.113 | 0.039 |
| 2.50 | 0.077 | 0.149 | 0.072 |
| 5.00 | 0.086 | 0.222 | 0.136 |
| 10.00 | 0.102 | 0.347 | 0.245 |
| 20.00 | 0.134 | 0.648 | 0.514 |

Example 4

A reagent A was prepared containing 70 mmol/l of sulfanilic acid, 200 mmol/l of glycine-HCl buffer so that the pH=3.1, 10 mmol/l of $Cu^{2+}$ and 0.15% w/v sodium dodecylsulfate. Separately a reagent B containing 200 mmol/l of $NaNO_2$ in water was prepared. The samples were taken from a pool of normal urines, and ditaurate bilirubin was added at concentrations of 0, 0.31, 0.62, 1.25, 2.5, 5, 10, and 20 mg/dl.

In a spectrophotometric cuvette 1 ml of water, 0.5 ml of the test sample and 1 ml of reagent A were admixed. The first photometric reading ($A_1$) was carried out at 620 nm, then 0.5 ml of reagent B was added. Seven seconds after the addition of reagent B, a second photometric reading ($A_2$) was carried out always at 620 nm. The difference between the two readings ($A_2-A_1$) was correlable to the concentration of bilirubin, at least up to 20 mg/dl as shown in the following Table 4.

TABLE 4

| ditaurate bilirubin (mg/dl) | $A_1$ | $A_2$ | $A_2$-$A_1$ |
|---|---|---|---|
| 0.00 | 0.160 | 0.162 | 0.002 |

TABLE 4-continued

| ditaurate bilirubin (mg/dl) | $A_1$ | $A_2$ | $A_2$-$A_1$ |
| --- | --- | --- | --- |
| 0.31 | 0.166 | 0.177 | 0.011 |
| 0.62 | 0.156 | 0.177 | 0.021 |
| 1.25 | 0.166 | 0.195 | 0.029 |
| 2.50 | 0.174 | 0.222 | 0.048 |
| 5.00 | 0.197 | 0.272 | 0.075 |
| 10.00 | 0.211 | 0.331 | 0.120 |
| 20.00 | 0.244 | 0.444 | 0.200 |

Example 5

A reagent A was prepared containing 90 mmol/l of sulfanilic acid, 400 mmol/l of acetic acid-sodium acetate buffer so that the pH=5.5, 3 mmol/l of $Cu^{2+}$ and 0.12% w/v triethanolamine laurylsulfate. Separately a reagent B containing 45 mmol/l of $NaNO_2$ in 50% of DMSO v/v water was prepared. The reagents A and B were admixed before the use in equal parts (single reagent C). The samples were taken from a pool of normal urines, and ditaurate bilirubin, was added at concentrations of 0, 0.31, 0.62, 1.25, 2.5, 5, 10, and 20 mg/dl.

In a spectrophotometric cuvette 1 ml of water, 0.5 ml of the test sample and 1 ml of the single reagent C were admixed. After 30 seconds the first photometric reading ($A_1$) was carried out at 610 nm; after five seconds, a second photometric reading ($A_2$) was carried out always at 610 nm. The difference between the two readings ($A_2-A_1$) was correlable to the concentration of bilirubin, at least up to 20 mg/dl as shown in the following Table 5.

TABLE 5

| ditaurate bilirubin (mg/dl) | $A_1$ | $A_2$ | $A_2$-$A_1$ |
| --- | --- | --- | --- |
| 0.00 | 0.136 | 0.136 | 0.000 |
| 0.31 | 0.137 | 0.144 | 0.007 |
| 0.62 | 0.125 | 0.138 | 0.013 |
| 1.25 | 0.131 | 0.158 | 0.027 |
| 2.50 | 0.135 | 0.186 | 0.051 |
| 5.00 | 0.143 | 0.262 | 0.099 |
| 10.00 | 0.167 | 0.333 | 0.166 |
| 20.00 | 0.169 | 0.400 | 0.231 |

Example 6

A reagent A was prepared containing 140 mmol/l of sulfanilic acid, 3 mmol/l of acetic acid-sodium acetate buffer so that the pH=3.8, 4.9 mmol/l of $Cu^{2+}$ and 0.28% w/v Triton X-100 ® (an octylphenoxy polyethoxyethanol surfactant) (Rohm & Haas Co.). Separately a reagent B containing 42 mmol/l of $NaNO_2$ in water was prepared. The samples were taken from a pool of normal urines and ditaurate bilirubin was added at concentrations of 0, 0.31, 0.62, 1.25, 2.5, 5, 10, and 20 mg/dl.

In a spectrophotometric cuvette 1.3 ml of water, 0.5 ml of the test sample and 0.4 ml of reagent A were admixed. The first photometric reading ($A_1$) was carried out at 635 nm, then 0.5 ml of reagent B was added. Ten seconds after the addition of reagent B, a second photometric reading ($A_2$) was carried out always at 635 nm. The difference between the two readings ($A_2-A_1$) was correlable to the concentration of bilirubin, at least up to 20 mg/dl as shown in the following Table 6.

TABLE 6

| ditaurate bilirubin (mg/dl) | $A_1$ | $A_2$ | $A_2$-$A_1$ |
| --- | --- | --- | --- |
| 0.00 | 0.370 | 0.370 | 0.000 |
| 0.31 | 0.370 | 0.380 | 0.010 |
| 0.62 | 0.380 | 0.400 | 0.020 |
| 1.25 | 0.370 | 0.420 | 0.050 |
| 2.50 | 0.380 | 0.470 | 0.090 |
| 5.00 | 0.380 | 0.570 | 0.190 |
| 10.00 | 0.390 | 0.780 | 0.390 |
| 20.00 | 0.395 | 1.235 | 0.840 |

Example 7

A reagent A was prepared containing 150 mmol/l of sulfanilic acid, 450 mmol/l of acetic acid-sodium acetate buffer so that the pH=5, 7 mmol/l of $Cu^{2+}$. Separately a reagent B containing 18.2 mmol/l of $NaNO_2$ in 0%, 37.5% and 75% v/v of DMSO in water was prepared. The samples were taken from a pool of normal urines and ditaurate bilirubin was added at concentrations of 0.6 and 10 mg/dl.

In a spectrophotometric cuvette 0.5 ml of water and 1 ml of the test sample, 0.5 ml of reagent A and 1 ml of reagent B were admixed. Five seconds after the addition of reagent B the first photometric reading ($A_1$) was carried out at 610 nm, then the time for a 50% increase in $A_1$ was measured.

In the following Table 7 it can be seen how the increase of the DMSO percentange in the reagent corresponds to a decrease of the initial reaction speed (1/t) with both 0.6 mg/dl and 10 mg/dl of bilirubin. This means that there is a proportionality between the concentration of DMSO and the time necessary to increase $A_1$ by 50%, i.e. an inverse proportionality between the concentration of DMSO and the reaction speed.

TABLE 7

| ditaurate bilirubin (mg/dl) | % DMSO | 1/t |
| --- | --- | --- |
| 0.6 | 0.0 | 65 |
|  | 12.5 | 8 |
|  | 25.0 | 1.9 |
| 10 | 0.0 | 70 |
|  | 12.5 | 22 |
|  | 25.0 | 9.5 |

COMPARATIVE EXAMPLE 8

Comparison Between the Specificity of the Reagent of the Invention and the One of Some Methods Employed at the Present By employing the reagents and the procedure of Example 6, four urine samples respectively having the following characteristics were analyzed:

Sample 1=clear appearance, straw-coloured
Sample 2=slightly turbid appearance, straw-coloured
Sample 3=clear appearance, light-yellow
Sample 4=turbid appearance, orange Samples 1 and 2 were analyzed because a clinical analysis laboratory obtained erroneous and strongly positive results by employing the "deep-and-read" method available at the present, in the absence of additional pathologic characteristics and in contrast to what was expected from the blood analysis which was normal. Samples 3 and 4 were analyzed as negative and positive controls.

The above-mentioned urine samples were analyzed by the following methods:
a) manual semi-quantitative method by reactive stripes COMBUR-9 ® (Boehringer Biochemia Robin);
b) manual semi-quantitative method by reactive stripes N-MULTISTIX ® (Ames-Miles);
c) automatic semi-quantitative method by reactive stripes URIFLET ® (Kyoto Daiichi) in a KYOTO URINE ANALYZER ® instrument (Kyoto Daiichi);
d) quantitative spectrophotometric method employing bilirubin oxidase, modified for the determination of bilirubin in the urine (see U.S. Pat. No. 4,571,383 and Doumas B. T., Perry B., Jenrzejczak B. and Davis L., Clin. Chem., 33, 1349, 1987);
e) Fouchet qualitative method (see Strasinger S. D., F. A. Davis Co. Philadelphia, 1985).

Methods a), b) and c) are diazo-coupling methods using dry reagents immobilized on reactive stripes, and are widely employed in most of the clinical analysis laboratories. Methods d) and e) were employed as reference and control; they are both based on oxidized bilirubin absorbance spectrum variations. Method d) uses the enzymatic oxidation of bilirubin, method e) uses the chemical oxidation of the same.

The analysis results of the four tested samples are set forth in the following Table 8.

TABLE 8

| Method | Samples | | | |
|---|---|---|---|---|
| | 1 | 2 | 3 | 4 |
| Example 6 (mg/dl) | 0.0 | 0.25 | 0.0 | 3.5 |
| COMBUR-9$^R$ | ++ | +++ | neg | +++ |
| N-MULTISTIX$^R$ | ++++ | ++++ | neg | +++ |
| URIFLET$^R$ | ++++ | ++++ | neg | +++ |
| Bil. oxidase (mg/dl) | 0.0 | 0.2 | 0.0 | 3.2 |
| Fouchet | neg | traces | neg | pos |

I claim:

1. A reagent for the detection and determination of bilirubin in urine, consisting essentially of a buffer suitable to maintain the pH of the reagent between 3 and 7 and inert to cupric ions, an aromatic compound selected from the group consisting of sulfanilic acid and sulfanilamide, a cupric soluble salt and an alkaline metal nitrite.

2. The reagent according to claim 1, wherein said buffer is selected from the group consisting of acetic acid-alkaline metal acetate, glycine-HCl and, alkaline metal formate-HCl.

3. The reagent according to claim 1, wherein said buffer is in a concentration between 10 mmol/l and 5,000 mmol/l, said aromatic compound is in a concentration between 5 mmol/l and 200 mmol/l, and said cupric salt is in a concentration between 1 mmol/l an 30 mmol/l and said nitrite is in a concentration between 10 mmol/l and 1,000 mmol/l.

4. The reagent according to claim 3, wherein said buffer is in a concentration of about 3,000 mmol/l, said aromatic compound is in a concentration of about 150 mmol/l, said cupric salt is in a concentration of 5 mmol/l and said nitrite is in a concentration of about 45 mmol/l.

5. A reagent for the detection and determination of bilirubin in urine, consisting essentially of a buffer suitable to maintain the pH of the reagent between 3 and 7 and inert to cupric ions, an aromatic compound selected from the group consisting of sulfanilic acid and sulfanilamide, a cupric soluble salt, an alkaline metal nitrite and a surfactant selected from the group consisting of anionic and non-ionic surfactants.

6. The reagent according to claim 5, wherein said surfactant is in a concentration between 0% and 10% w/v.

7. The reagent according to claim 6, wherein said surfactant is in a concentration of about 0.3% w/v.

8. The reagent according to claim 5, wherein said surfactant is selected from the group consisting of octylphenoxy polyethoxyethanols, polyoxyethylene alcohols, sodium dodecylsulfate and triethanolamine laurylsulfate.

9. The reagent according to claim 5, wherein said surfactant is an octylphenoxy polyethoxyethanol.

10. The reagent according to claims 1 or 5, further comprising dimethylsulfoxide.

11. The reagent according to claim 10, wherein dimethylsulfoxide is in a concentration between 0% and 100% w/v.

12. The reagent according to claim 11, wherein dimethylsulfoxide is in a concentration of about 50% w/v.

* * * * *